(12) United States Patent
Minoguchi et al.

(10) Patent No.: US 8,708,989 B2
(45) Date of Patent: Apr. 29, 2014

(54) TAMPON COMPRISING A PLURALITY OF STRIPS OR CORDS

(75) Inventors: Ryo Minoguchi, Blue Ash, OH (US); John Lawrence Foley, Liberty Township, OH (US); Ricky Alan Pollard, Moscow, OH (US); David Joseph Caracci, Evendale, OH (US); Thomas Ward Osborn, III, Clifton, OH (US); Diana Lynne Gann, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 137 days.

(21) Appl. No.: 13/346,150

(22) Filed: Jan. 9, 2012

(65) Prior Publication Data
US 2012/0109089 A1    May 3, 2012

Related U.S. Application Data

(62) Division of application No. 10/836,892, filed on Apr. 30, 2004, now abandoned.

(51) Int. Cl.
*A61F 13/15*    (2006.01)
(52) U.S. Cl.
USPC .................................... 604/385.18
(58) Field of Classification Search
USPC ............ 604/385.17, 385.18; 424/430, 431
See application file for complete search history.

(56) References Cited

U.S. PATENT DOCUMENTS

| | | |
|---|---|---|
| 2,905,175 A | 9/1959 | Schwartz |
| 3,085,574 A | 4/1963 | Penkes |
| 3,320,956 A | 5/1967 | Steiger |
| 3,397,695 A | 8/1968 | Voss |
| 3,593,715 A | 7/1971 | Merrill |
| 3,981,305 A | 9/1976 | Ring |
| 4,335,721 A | 6/1982 | Matthews |
| 5,112,348 A | 5/1992 | Glassman et al. |
| 5,364,383 A | 11/1994 | Hayes |
| 5,584,827 A | 12/1996 | Korteweg |
| 6,458,456 B1 | 10/2002 | Zainiev et al. |
| 2003/0191443 A1 | 10/2003 | Taylor et al. |
| 2005/0256482 A1 | 11/2005 | Minoguchi et al. |

FOREIGN PATENT DOCUMENTS

FR    2 340 084 A    9/1977

OTHER PUBLICATIONS

PCT International Search Report dated Oct. 10, 2005.

*Primary Examiner* — Melanie Hand
(74) *Attorney, Agent, or Firm* — Wednesday G. Shipp; Andrew J. Hagerty

(57) ABSTRACT

A tampon that has a body including a first end, a second end, a center portion, a longitudinal axis and a radial axis. The body includes a plurality of cords or strips joined at the first end, the second end, the center portion or both the first and second ends. The plurality of strips and cords being selected from the group being selected from the group consisting of, films, woven materials, absorbent foams, superabsorbent polymers, and mixtures thereof.

14 Claims, 4 Drawing Sheets

TAMPON COMPRISING A PLURALITY OF STRIPS OR CORDS

CROSS REFERENCE TO RELATED APPLICATION

This application is a divisional of U.S. application Ser. No. 10/836,892 filed Apr. 30, 2004 now abandoned.

FIELD OF THE INVENTION

This invention relates to a tampon comprising a plurality of cords or strips joined at the first end, the second end, the center portion, or both the first end and second end.

BACKGROUND OF THE INVENTION

A wide variety of absorbent catamenial tampons have long been known in the art. It is well known that the primary function which tampons provide is leakage protection, that is, preventing menstrual discharges from leaking out of body onto an undergarment. The absorbency of tampons is generally regulated and categorized publicly so that consumers can select a tampon with appropriate absorbency in accordance with their expected level of menstrual flow. However, even when consumers have chosen the absorbency correctly, it has been found that even the best tampons do not prevent unexpected leakage. This unexpected leakage is commonly called "bypass" failure, which occurs when the menses travels in the space between the vagina and the tampon and the tampon fails to intercept the flowing menses due to lack of total coverage of the vagina by the tampon. Because bypass failure imposes unpredictability and persistent fear of leakage to consumers, it is considered unacceptable and an effective solution has been long desired by consumers.

It is an object of the present invention to provide a tampon that improves coverage and solves the problem of bypass failure. The body of the tampon of the present invention comprises a plurality of cords or strips joined at the first end, the second end, the center portion, or both the first end and second end. Not to be bound by theory, the inventors believe the nature of materials chosen to comprise the body of the tampon enable the strips or cords to exhibit improved deformation and spreading within the vagina over known tampons comprised of separate filaments and fibers, as described in for example U.S. Pat. No. 3,320,956 issued to Steiger on May 23, 1967 and U.S. Pat. No. 4,335,721 issued to Matthews on Jun. 22, 1982. Moreover, the nature of the materials that comprise the body of the tampon provide sufficient void volume for absorbency. It is believed that the tampon of the present invention provides significant improvement of the coverage and solves the problem of bypass failure.

SUMMARY OF THE INVENTION

This invention relates to a tampon having a body comprising a first end, a second end, and a center portion. The body includes a plurality of cords or strips joined at the first end, the second end, the center portion or both the first and second end. The plurality of strips and cords being selected from the group being selected from the group consisting of, films, woven materials, absorbent foams, superabsorbent polymers, and mixtures thereof.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

As used herein "applicator" refers to a device or implement that facilitates the insertion of a tampon, medicament, treatment device, visualization aid, or other into an external orifice of a mammal, such as the vagina, rectum, ear canal, nasal canal, or throat. Non-limiting specific examples of such include any known hygienically designed applicator that is capable of receiving a tampon may be used for insertion of a tampon, including the so-called telescoping, tube and plunger, and the compact applicators, an applicator for providing medicament to an area for prophylaxis or treatment of disease, a spectroscope containing a microcamera in the tip connected via fiber optics, a speculum of any design, a tongue depressor, a tube for examining the ear canal, a narrow hollow pipe for guiding surgical instruments, and the like.

The term, "cords," as used herein, refers to a long slender flexible material consisting of several strips of material woven or twisted together.

The term "digital tampon," as used herein, refers to a tampon which is intended to be inserted into the vaginal canal with the user's finger and without the aid of an applicator. Thus, digital tampons are typically visible to the consumer prior to use rather than being housed in an applicator.

The term "joined" or "joined," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

Figure 1:
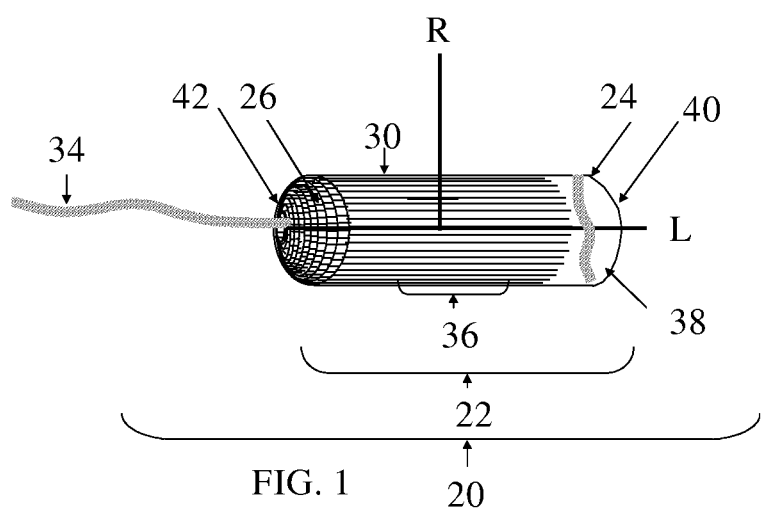
FIG. 1 is a plan view of a tampon of the present invention comprising a plurality of strips joined at the first end which corresponds with the withdrawal end.

As used herein, the term "longitudinal axis" of a tampon refers to the axis that runs through the center of the tampon as shown in FIG. 1. A portion of the tampon may be asymmetric about the longitudinal axis, such as when the withdrawal end region is flared and distorted from the original shape of the rest of the tampon (such as a "fin shape"). Further, the longitudinal axis may be linear or non-linear.

As used herein, the term "radial axis" of a tampon refers to the axis that runs at right angles to the longitudinal axis of the tampon as shown in FIG. 1.

The term "rolled," as used herein, is the configuration of the body of the tampon after winding the absorbent material upon itself.

As used herein, the term "tampon," refers to any type of absorbent structure that is inserted into the vaginal canal or other body cavities for the absorption of fluid therefrom, to aid in wound healing, or for the delivery of active materials, such as medicaments, or moisture.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring), and the cervix. The terms "vaginal cavity," "within the vagina" and "vaginal interior," do not include the interlabial space, the floor of vestibule or the externally visible genitalia.

Figure 2:
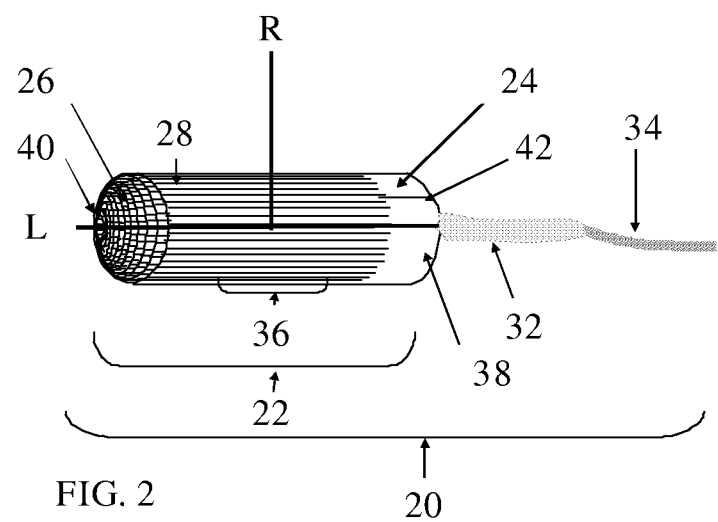
FIG. 2 is a plan view of a tampon of the present invention comprising a plurality of strips joined at the first end which corresponds with the insertion end.

The tampons 20 illustrated in FIG. 1 and FIG. 2 resemble a tassel. FIG. 1 illustrates a tampon 20 comprising a body 22 that comprises a first end 24 with a joined portion 38, a second end 26, a center portion 36, a withdrawal member 34 a radial axis R, and a longitudinal axis L. The body 22 of the tampon 20 comprises a plurality of strips 30 joined at the joined portion 38 which is, located at the first end 24. The tampon 20 also comprises a withdrawal member 34 that extends though the middle of the body 22 of the tampon 22 and forms the withdrawal member 34. The plurality of strips 30 being selected from the group being selected from the group consisting of, films, woven materials, absorbent foams, superabsorbent polymers, and mixtures thereof. FIG. 1 shows a configuration of the tampon 20 in which the first end 24 may be considered the insertion end 40 of the tampon.

FIG. 2 illustrates a tampon 20 comprising a body 22 that comprises a first end 24 with a joined portion 38, a second end 26, a center portion 36 a withdrawal member 34 a radial axis R, and a longitudinal axis L. The body 22 of the tampon 20 comprises a plurality of cords 28 joined at the joined portion 38 which is located at the first end 24. The tampon 20 also comprises a withdrawal member 34 and secondary absorbent member 32. The plurality of cords 28 being selected from the group being selected from the group consisting of, films, woven materials, absorbent foams, superabsorbent polymers, and mixtures thereof. FIG. 2 shows a configuration in which the first end 24 may be considered the withdrawal end 42 of the tampon 20.

Figure 3:
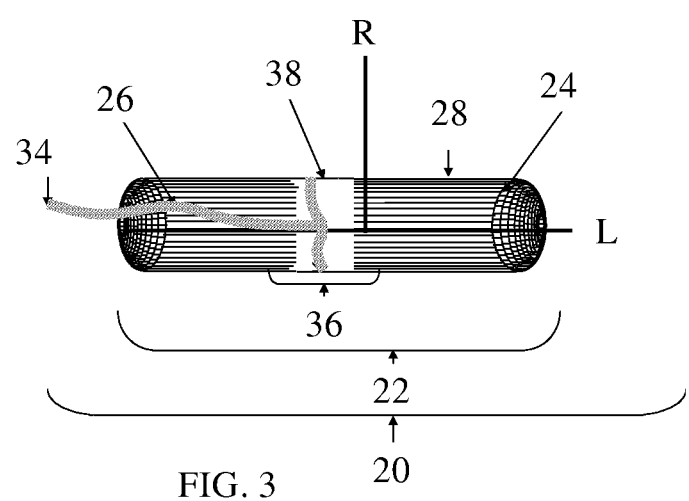
FIG. 3 is a plan view of a tampon of present invention comprising a plurality of cords joined at the center portion of the tampon.

The tampon 20 illustrated in FIG. 3 resembles a "pompom." FIG. 3 is a plan view of tampon 20 of present invention, in which the tampon 20 comprising a body 22 that comprises a first end 24, a second end 26, a center portion 36 comprising a joined portion 38, a withdrawal member 34 a radial axis R, and a longitudinal axis L. The tampon 20 is configured such that the body 22 a plurality of cords 28 are joined at the joined portion 38 located at the center portion 36 of the tampon 20. The plurality of cords 28 being selected from the group being selected from the group consisting of, films, woven materials, absorbent foams, superabsorbent polymers, and mixtures thereof.

Figure 4:
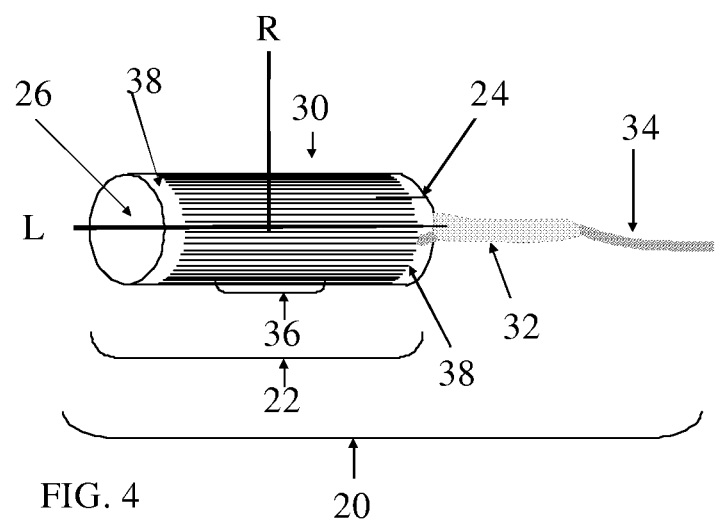
FIG. 4 is a plan view of a tampon of the present invention comprising a plurality of strips fused at both the first end and the second end.

The tampon 20 illustrated in FIG. 4 resembles a "Chinese Lantern." FIG. 4 is a plan view of tampon 20 of present invention, comprising a body 22 that comprises a first end 24 comprising a joined portion 38, a second end 26 comprising a joined portion, a center portion 36 comprising a joined portion 38 a withdrawal member 34 a radial axis R, and a longitudinal axis L. The tampon 20 is configured such that the body 22 of the tampon 20 comprises a plurality of strips 30 in the center portion 36 joined at both of the joined portions 28 located at the first end 24 and the second end 26. The plurality of strips 30 being selected from the group being selected from the group consisting of, films, woven materials, absorbent foams, superabsorbent polymers, and mixtures thereof. FIG. 4 also comprises a secondary absorbent member 32.

The body 22 of the tampon 20 may be constructed from a wide variety of liquid-absorbing materials commonly used in absorbent articles. The absorbent materials may be two dimensional and have a thickness of up to 2 mm. Such materials include but are not limited to nonwoven materials, films, woven materials, absorbent foams (such as those disclosed in U.S. Pat. No. 3,994,298 issued to DesMarais on Nov. 30, 1976 and U.S. Pat. No. 5,795,921 issued to Dyer, et al.), cellulose sponge, capillary channel fibers (such as those disclosed in U.S. Pat. No. 5,356,405 issued to Thompson, et. al on Oct. 18, 1994), high capacity fibers (such as those disclosed in U.S. Pat. No. 4,044,766 issued Kaczmarzk, et al. on Aug. 30, 1977), superabsorbent polymers or absorbent gelling materials (such as those disclosed in U.S. Pat. No. 5,830,543 issued to Miyake, et al. on Nov. 3, 1998), and mixtures thereof. The body 22 may be treated to be hydrophilic. The nonwoven materials may comprise any natural fibers, any synthetic fibers, or mixtures thereof. The nonwoven materials may comprise cellulosic fibers such as cotton, cotton linter, rayon, cuprammonium rayon, viscose rayon, pulp and the like. Such nonwoven materials are available from Asahi Kasei Corporation, Osaka, Japan, under the trade name of BEMLIESE or BEMCOT, and from Futamura Chemical Co., Ltd., Gifu, Japan, under the trade name of TAIKO TCF.

The tampon's 20 length can be measured from the first end 24 to the second end 26 along the longitudinal axis L. A typical tampon for human use is 30-60 mm in length. The tampon 20 may be less than about 60 mm in length or may be less than about 55 mm in length. The tampon 20 may be straight or non-linear in shape, such as curved along the longitudinal axis. A typical tampon is 8-20 mm wide. The width of the tampon 20 may be less than about 17 mm or may be less than about 15 mm. The width of a tampon 20 unless otherwise stated in the specification, corresponds to the length across the largest cylindrical cross-section along the length of the tampon.

The body 22 includes either a plurality of cords 28 or strips 30 joined at the joined portion 28. The body 22 may be made and any way known to those skilled in the art of passementerie. The joined portion 38 may comprised at one or more locations on the body 22 of the tampon 20. The first end 24 may comprise a joined portion 38, the second end 26 may comprise a joined portion 38, and the center portion 36 has a joined portion 38. Alternatively, both the first end 24 and the second end 26 may comprise a joined portion 38. The joined portion 38 may be integral or may joined by means known in that including but not limited to sewing, adhesive attachment, bonding, thermal bonding, ultrasonic bonding or a combination thereof. The joined portion 38 may have a length of from about 2 mm to about 10 mm in length.

Each of the cords 28 or strips 30 have a length ranging from about 20 mm to about 60 mm. The plurality of the cords 28 or strips 30 may have a length that is equidistant from the first end 24. Alternatively, each of the cords 28 and strips 30 may have a different length from another cord 28 and strip 30. For example, the plurality of cords 28 and strips 30 may be configured such that the cords 28 and strips 30 may be longer on the longitudinal axis L and shorter on the perimeter. The plurality of cords 28 or strips 30 have a width ranging from about 0.5 mm to about 5 mm. The cords 28 or strips 30 may be crimped or twisted. The cords 28 or strips 30 may have various shapes selected from the group consisting of round edged, zigzag lined, wavy lined, H shaped, C shaped, T shaped, V shaped and mixtures thereof.

The tampon 20 may have both cords 28 and strips 30 comprising the body 22. The cords 28 or strips 30 may be uncut or "looped" at ends not comprising a joined portion 38.

An example may be a body 22 of a tampon 20 comprising looped cords 28 or strips 30 having a side profile that resembles a "figure eight." Tampons 20 with this configuration can be made by utilizing a fixture that consists of two stainless steel dowels pins, ⅛" diameter by 3" long, pressed into holes spaced 2" apart in an aluminum block. The strips 30 or cords 28 are wrapped around the pins to form the "figure eight."

The tampon 20 of the present invention may optionally comprise an overwrap comprising material such as rayon, cotton, bicomponent fibers, polyethylene, polypropylene, other suitable natural or synthetic fibers known in the art, and mixtures thereof. The tampon 20 may have a nonwoven overwrap comprised of bicomponent fibers that have a polypropylene core surrounded by polyethylene manufactured by Vliesstoffwerke Christian Heinrich Sandler GmbH & Co. KG (Schwarzenbach/Saale, Germany) under the tradename SAS B31812000. The tampon 20 may comprise a nonwoven overwrap of a hydroentangled blend of 50% rayon, 50% polyester available as BBA 140027 produced by BBA Corporation of South Carolina, U.S. The overwrap may be 100% polyester. The overwrap may be treated to be hydrophilic, hydrophobic, wicking or non-wicking. The tampon pledget may also contain a variety of other adjuvants such as lubricants, odor control agents, antibacterial agents, colorants, indicators or medicaments for various kinds of illnesses such as yeast infections, indicator features for signaling when the tampon should be changed, and the like.

The tampon 20 of the present invention may comprise a secondary absorbent member 32. The secondary absorbent member may be comprised of material such as rayon, cotton, bicomponent fibers, polyethylene, polypropylene, polyester, other suitable natural or synthetic fibers known in the art, and mixtures thereof. The secondary absorbent member may be single ply or multiple plies. The secondary absorbent member 32 may be absorbent and/or hydrophilic. The secondary absorbent member 32 may be joined to the first end 24 of the body 22 of the tampon. The secondary absorbent member 32 may be arranged in a wide variety of shapes and configurations and may be generally cylindrical, spherical, semi-spherical, disc-like, planar, rectangular, "sheet-like," "skirt-like" in shape. The secondary absorbent member 32 may range in length from about 10 mm to about 40 mm from the withdrawal end 42 of the tampon 20. The secondary absorbent member 32 may be from about 20 mm to about 25 mm in length, from about 6 mm to about 40 mm in width, and from about 0.5 mm to about 5 mm in thickness.

Withdrawal members 34 useful in the present invention may be made of any suitable material known in the prior art and include cotton and rayon. In addition, the withdrawal member 32 can take on other forms such as a ribbon, loop, tab, or the like. The withdrawal member 34 may be comprised of cords 28 or strips 30 of material. The withdrawal member 34 may be integral with the tampon pledget. Alternatively, the withdrawal member 34 is joined at the first end 24 of the tampon. If the first end 24 of the tampon 20 is considered the insertion end the withdrawal member 34 may be joined such that the withdrawal member 34 is located in the center of the cords 28 or strips. Moreover, the withdrawal member 34 may be joined to the entire thickness of the body 22 or only part of the thickness of the body 22. The withdrawal member 34 or regions of the withdrawal member 34 may be treated to be non-absorbent, absorbent or hydrophilic. The withdrawal member 34 may be joined in any suitable manner known in the art including sewing, adhesive attachment, bonding, thermal bonding, or a combination thereof including the method disclosed in currently pending, commonly assigned, U.S. patent application Ser. No. 10/610,075, filed Jun. 30, 2003, entitled "Method and Apparatus for Cord Attachment" to Sargent, et al.

The tampon 20 of the present invention may be inserted digitally. It may be desirable to provide a finger indent at the withdrawal end 26 of the tampon 20 to aid in insertion, if the tampons 20 are to be digital tampons. An example of a finger indent can be found in U.S. Pat. No. 6,283,952, filed May 5, 1997, entitled "Shaped Tampon," issued to Child, et al.

Alternatively, the insertion may be aided through the use of any applicator known in the prior art. Prior art applicators having a typical "tube and plunger" type arrangement may be plastic, paper, or other suitable material. Additionally, a "compact" type applicator is also suitable.

While several methods of making the tampon 20 of the present invention should be apparent to one of skill in the art in light of the disclosure herein, following is a description of one method of making a tampon 20 of the present invention.

The tampon 20 of the present invention is made by providing the material that comprises the body 22. The starting material for the body 22 of the tampon 20 may comprise a plurality of strips 30, a plurality of cords 28, a sheet of material that may be cut in strips 30, or may be a material that is formed in a mold to achieve the intended shape. If the starting material comprises a plurality of strips 30 or cords 28, the strips 30 and cords 28 may be joined together at the joined portion 38 of first end 24, the center portion 36 or both the first end 24 and the second end 26. The plurality of strips 30 may joined by means known in that including but not limited to tying, knotting, sewing, adhesive attachment, bonding, thermal bonding, ultrasonic bonding or a combination thereof. If the starting material of the body 22 of the tampon 20 comprises a sheet of material, the sheet of material may be cut into a plurality of strips 30 by any means known in the art including but not limited to scissors, shears, razor, laser, and mixtures thereof. Tampons 20 that comprise a plurality of strips 30 may be further transformed into a plurality cords 28 by twisting two or more strips 30 together to form a cord. Another method of making the body 22 of the tampon 20 may include pouring a starting material into a mold with a plurality of holes.

After the body 22 of the tampon 20 is made, the withdrawal member 34 is provided. The withdrawal member 32 may be joined to the first end 24 of the body in any suitable manner known in the art including sewing, adhesive attachment, bonding, thermal bonding, or a combination thereof, including the method disclosed in currently pending, commonly assigned, U.S. patent application Ser. No. 10/610,075, filed Jun. 30, 2003, entitled "Method and Apparatus for Cord Attachment" to Sargent, et al. Optionally, a secondary absorbent 32 is provided if the first end 24 of the tampon 20 corresponds to the withdrawal end 26. The secondary absorbent 32 may be joined to the first end 24 of the body in any suitable manner known in the art including sewing, adhesive attachment, bonding, thermal bonding, or a combination thereof. Optionally, the tampon 20 of the present invention may be positioned within an applicator, which is subsequently wrapped.

EXAMPLE 1

A tampon 20 of the present invention is made similar to that shown in FIG. 1. The material that comprises the body 22 of the tampon 20 is provided. The material that comprises the body 22 of the tampon 20 is cuprammonium rayon nonwoven material available from Ashahi Kasei Corporation, Osaka, Japan, under the trade name of BEMLIESE TF603. The basis weight of the material is 60 g/m². The material that comprises the body 22 is then cut into a rectangle which is 50 mm long and 500 mm wide. The material that comprises the body 22 is then cut into a plurality of strips 30 along the longitudinal axis L using a ruler die comprising a plurality of blades. The strips 30 are 40 mm long and 1 mm wide. The material that comprises the body 22 is then rolled into a cylindrical shape of about 14 mm in diameter. The material that comprises the body 22 is next tied at the non-slit end with a cotton yarn available from Wehadkee Yarn Mills, West Point, Ga., under the code name of WYMAC7309A. The cotton yarn is then pushed though the center of the body 22 of the tampon 22 and forms the withdrawal member 34. The tampon 20 is then either placed in an applicator or digitally inserted so that the strips 30 are at the withdrawal end 42 of the tampon.

EXAMPLE 2

A tampon 20 of the present invention is made similar to that shown in FIG. 2. The material that comprises the body 22 of the tampon 20 is provided. The material that comprises the body 22 of the tampon 20 is cuprammonium rayon nonwoven material available from Ashahi Kasei Corporation, Osaka, Japan, under the trade name of BEMLIESE TF103. The basis weight of the material is 100 g/m². The material that comprises the body 22 is then cut into a rectangle which is 50 mm long and 300 mm wide. The material that comprises the body 22 is then cut into a plurality of strips 30 along the longitudinal axis L using a ruler die comprising a plurality of blades. The strips 30 are 40 mm long and 2 mm wide. The material that comprises the body 22 is then rolled into a cylindrical shape of about 14 mm in diameter. The material that comprises the body 22 is next tied at the non-slit end with a cotton yarn available from Wehadkee Yarn Mills, West Point, Ga., under the code name of WYMAC7309A. The cotton yarn forms the withdrawal member 34. The tampon 20 is then either placed in an applicator or digitally inserted so that the strips 30 are at the insertion end 40 of the tampon.

EXAMPLE 3

A tampon 20 of the present invention is made similar to that shown in FIG. 2. The material that comprises the body 22 of the tampon 20 is provided. The material that comprises the body 22 of the tampon 20 is a viscose rayon nonwoven material available from Futamura Chemical Co., Ltd., Gifu, Japan, under the trade name of TAIKO TCF408. The basis weight of the material is 80 g/m². The material that comprises the body 22 is then cut into a rectangle which is 50 mm long and 375 mm wide. The material that comprises the body 22 is then cut into a plurality of strips 30 along the longitudinal axis L using a ruler die comprising a plurality of blades. The strips 30 are 40 mm long and 1 mm wide. Next, the strips 30 are twisted together to form cords 28. The material that comprises the body 22 is then rolled into a cylindrical shape of about 14 mm in diameter. The material that comprises the body 22 is next tied at the non-slit end with a cotton yarn available from Wehadkee Yarn Mills, West Point, Ga., under the code name of WYMAC7309A. The cotton yarn forms the withdrawal member 34. The tampon 20 is then either placed in an applicator or digitally inserted so that the strips 30 are at the insertion end 40 of the tampon.

EXAMPLE 4

A tampon 20 of the present invention is made similar to that shown in FIG. 3. The material that comprises the body 22 of the tampon 20 is provided. The material that comprises the body 22 of the tampon 20 is a viscose rayon nonwoven material available from Futamura Chemical Co., Ltd., Gifu, Japan, under the trade name of TAIKO TCF408. The basis weight of the material is 80 g/m². The material that comprises the body 22 is then cut into a rectangle which is 50 mm long and 375 mm wide. The material that comprises the body 22 is then cut into a plurality of strips 30 along the longitudinal axis L from the both ends using a ruler die comprising a plurality of blades. The strips 30 are 20 mm long and 1 mm wide. Next, the strips 30 or material are than twisted together to form cords 28. The material that comprises the body 22 is then rolled into a cylindrical shape of about 14 mm in diameter. The material that comprises the body 22 is next tied at the center portion of the body 22 with a cotton yarn available from Wehadkee Yarn Mills, West Point, Ga., under the code name of WYMAC7309A. The cotton yarn forms the withdrawal member 34. The tampon 20 is then either placed in an applicator or digitally inserted so that the strips 30 are at the insertion end 40 of the tampon.

EXAMPLE 5

A tampon 20 of the present invention is made similar to that shown in FIG. 1. The material that comprises the body 22 of the tampon 20 is provided. The material that comprises the body 22 of the tampon 20 is cuprammonium rayon nonwoven material available from Ashahi Kasei Corporation, Osaka, Japan, under the trade name of BEMLIESE TF603. The basis weight of the material is 60 g/m². The material that comprises the body 22 is then cut into is cut into a rectangle of which is 50 mm long and 500 mm wide. The material that comprises the body 22 is then cut into a plurality of strips 30 along the longitudinal axis L starting and ending 5 mm inside from the width sides to form strips using a ruler die comprising a plurality of blades. The strips 30 are cut 40 mm long and 1 mm wide. The material that comprises the body 22 is then into a cylindrical shape of about 14 mm in diameter. The material that comprises the body 22 is then is next tied at both of the non-slit end with a cotton yarn available from Wehadkee Yarn Mills, West Point, Ga., under the code name of WYMAC7309A. The cotton yarn forms the withdrawal member 34. The tampon 20 is then either placed in an applicator or digitally inserted so that the strips 30 are at the insertion end 40 of the tampon.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:
1. A tampon comprising an insertion end and a withdrawal end:
   said tampon comprising a body comprising a first end, and a second end;
   said first end comprising a joined portion;
   said body comprising a plurality of strips joined at said joined portion at said first end;

wherein said strips being selected from the group consisting of films, woven materials, absorbent foams, superabsorbent polymers, and mixtures thereof, and wherein said strips are configured into cords.

2. The tampon according to claim 1 further comprising a secondary absorbent.

3. The tampon according to claim 1 wherein said second end comprises a joined portion and said plurality of strips are joined at said joined portion at said second end.

4. A tampon comprising an insertion end and a withdrawal end:

said tampon comprising a body comprising a first end and a second end;

said first end comprising a joined portion;

said body comprising a plurality of cords joined at said joined portion at said first end; wherein said cords being selected from the group consisting of nonwoven materials, films, woven materials, absorbent foams, superabsorbent polymers, and mixtures thereof.

5. The tampon according to claim 4 wherein said joined portion has a length of from about 2 mm to about 10 mm.

6. The tampon according to claim 4 wherein said plurality of cords have a length ranging from about 20 mm to about 60 mm.

7. The tampon according to claim 4 wherein said first end comprises said insertion end.

8. The tampon according to claim 4 wherein said first end comprises said withdrawal end.

9. The tampon according to claim 4 further comprising a secondary absorbent.

10. The tampon according to claim 4 wherein said second end comprises a joined portion and said plurality of cords are joined at said joined portion at said second end.

11. A tampon comprising an insertion end and a withdrawal end:

said tampon comprising a body comprising a center portion comprising a joined portion;

said body comprising a plurality of strips joined at said joined portion of said center portion; wherein said strips being selected from the group consisting of nonwoven materials, films, woven materials, absorbent foams, superabsorbent polymers, and mixtures thereof and wherein said strips are configured into cords.

12. The tampon according to claim 11 wherein said joined portion has a length of from about 2 mm to about 10 mm.

13. The tampon according to claim 11 wherein said plurality of strips have a length ranging from about 20 mm to about 60 mm.

14. A tampon comprising an insertion end and a withdrawal end:

said tampon comprising a secondary absorbent and a body comprising a center portion comprising a joined portion;

said body comprising a plurality of strips joined at said joined portion of said center portion;

wherein said strips being selected from the group consisting of nonwoven materials, films, woven materials, absorbent foams, superabsorbent polymers, and mixtures thereof.

* * * * *